United States Patent
Kum et al.

(10) Patent No.: US 11,331,416 B2
(45) Date of Patent: May 17, 2022

(54) METHOD FOR MANUFACTURING STENT FOR INHIBITING WEBBING PHENOMENON

(71) Applicant: OSSTEM CARDIOTEC CO., LTD., Seoul (KR)

(72) Inventors: Chang Hun Kum, Seoul (KR); Kwang Soo Kim, Gimpo-si (KR); Bunam Chang, Guri-si (KR); Jae Hwa Cho, Seoul (KR); Sung Nam Kang, Seoul (KR); Gyu Hyun Jin, Seoul (KR); Hye Young Kwon, Namyangju-si (KR); Ji Seon Hong, Daejeon (KR); Saet Byeol Kim, Guri-si (KR)

(73) Assignee: OSSTEM CARDIOTEC CO., LTD., Seoul (KR)

( * ) Notice: Subject to any disclaimer, the term of this patent is extended or adjusted under 35 U.S.C. 154(b) by 0 days.

(21) Appl. No.: 17/265,262

(22) PCT Filed: May 27, 2019

(86) PCT No.: PCT/KR2019/006298
§ 371 (c)(1),
(2) Date: Feb. 2, 2021

(87) PCT Pub. No.: WO2020/027414
PCT Pub. Date: Feb. 6, 2020

(65) Prior Publication Data
US 2021/0308340 A1 Oct. 7, 2021

(30) Foreign Application Priority Data
Aug. 3, 2018 (KR) .......................... 10-2018-0090869

(51) Int. Cl.
*B05D 3/02* (2006.01)
*A61L 24/02* (2006.01)
(Continued)

(52) U.S. Cl.
CPC ............. *A61L 31/022* (2013.01); *A61L 31/10* (2013.01); *A61L 31/16* (2013.01); *A61L 2420/02* (2013.01)

(58) Field of Classification Search
CPC ............................ B05D 3/0218; B05D 1/002
See application file for complete search history.

(56) References Cited

U.S. PATENT DOCUMENTS 6,818,247 B1 * 11/2004 Chen ........................ A61L 27/34
427/2.1
7,211,150 B1 * 5/2007 Kokish ............... B05B 13/0242
118/320
(Continued)

FOREIGN PATENT DOCUMENTS

JP       2005168937       6/2005
KR       20080041209      5/2008
(Continued)

OTHER PUBLICATIONS

International Search Report—PCT/KR2019/006298 dated Aug. 22, 2019.
(Continued)

*Primary Examiner* — Cachet I Proctor
(74) *Attorney, Agent, or Firm* — Cantor Colburn LLP

(57) ABSTRACT

Provided is a method for manufacturing a stent, including: coating a coating material on a stent; and drying the stent at a temperature in the range of from 40° C. to 150° C., and the coating and the drying are simultaneously performed.

8 Claims, 6 Drawing Sheets

(51) Int. Cl.
*A61L 31/02* (2006.01)
*A61L 31/10* (2006.01)
*A61L 31/16* (2006.01)

(56) References Cited

U.S. PATENT DOCUMENTS

| | | | | |
|---|---|---|---|---|
| 7,396,556 | B2* | 7/2008 | Hayes | B05B 13/0214 |
| | | | | 118/319 |
| 7,504,125 | B1* | 3/2009 | Pacetti | B05D 3/0466 |
| | | | | 427/2.24 |
| 7,645,476 | B2* | 1/2010 | Verlee | B05C 13/025 |
| | | | | 427/2.24 |
| 7,858,143 | B2* | 12/2010 | Hossainy | B05D 1/002 |
| | | | | 427/2.24 |
| 8,187,661 | B2* | 5/2012 | Madriaga | B05B 13/0235 |
| | | | | 427/2.24 |
| 8,741,378 | B1* | 6/2014 | Roorda | A61K 31/439 |
| | | | | 427/2.24 |
| 2006/0029720 | A1* | 2/2006 | Panos | B05D 1/26 |
| | | | | 427/2.1 |
| 2007/0031611 | A1 | 2/2007 | Babaev | |
| 2014/0193569 | A1* | 7/2014 | Huang | A61L 31/10 |
| | | | | 427/2.25 |

FOREIGN PATENT DOCUMENTS

| | | |
|---|---|---|
| KR | 20120117169 | 10/2012 |
| KR | 20150083732 | 7/2015 |
| KR | 101709628 | 2/2017 |

OTHER PUBLICATIONS

Korean Office Action—Korean Application No. 10-2018-0090869 dated Jan. 13, 2020, citing KR 10-2012-0117169 and KR 10-2008-0041209.

* cited by examiner

METHOD FOR MANUFACTURING STENT FOR INHIBITING WEBBING PHENOMENON

TECHNICAL FIELD

The present disclosure relates to a method for manufacturing a stent for inhibiting a webbing phenomenon.

BACKGROUND

Stents are luminal dilatation devices used to widen passageways narrowed by coarctation and are widely used for the treatment of cancers or vascular diseases.

The stents can be generally classified into metal stents and drug eluting stents each having a coating layer containing a therapeutic substance. The drug eluting stents are coated with a polymer as well as a therapeutic substance to reduce physiological side effects of stent interventions for restenosis and late blood clots.

When a drug layer of a drug eluting stent is coated with a material such as a polymer, it is very difficult to uniformly and/or evenly coat the surface of the stent due to a specific shape and structure of the stent and insufficient coating techniques and methods. In addition, when the surface of a metal stent is coated with a coating solution (hereinafter, referred to as "coating material") in which a polymer, a drug and a solvent are mixed, the coating material in a liquid state flows and the solution stagnates in a bent cell portion of the stent (hereinafter, referred to as "bent portion"). Here, the bent portion is coated abnormally thick, and this phenomenon is referred to as "webbing". In addition, the flow of the coating material refers to a phenomenon that the coating material flows on the stent together with the solvent, for example, when the stent is coated with the solution containing the polymer and the drug having a concentration of 0.1% to 70%.

Meanwhile, the bent cell portion of the stent is coated thick with the coating solution, i.e., the webbing phenomenon occurs. Due to this webbing phenomenon, blood clots in the body may easily stick to the stent and the thick coating material contains an excessive amount of drugs that inhibit physiological side effects and thus causes cytotoxicity.

In addition, the decomposition rate of the coating layer of the drug eluting stent thickened by the webbing phenomenon is reduced so that the recovery rate of blood vessels can also be reduced.

An example of the background technology of the present disclosure is Korean Patent Laid-open Publication No. 10-2008-0041209 which relates to an ultrasonic medical stent coating method and device. However, the above-described patent is limited to coating of a stent by using ultrasound energy, but does not describe inhibiting of a webbing phenomenon.

DISCLOSURE OF THE INVENTION

Problems to be Solved by the Invention

In view of the foregoing, the present disclosure provides a stent and a method for manufacturing the same.

However, problems to be solved by the present disclosure are not limited to the above-described problems. There may be other problems to be solved by the present disclosure.

Means for Solving the Problems

As a technical means for solving the above-described technical problems, a first aspect of the present disclosure provides a method for manufacturing a stent, including: coating a coating material on a stent; and drying the stent at a temperature in the range of from 40° C. to 150° C., and the coating and the drying are simultaneously performed.

According to an embodiment of the present disclosure, the coating and the drying may be simultaneously performed to inhibit a webbing phenomenon, but may not be limited thereto.

According to an embodiment of the present disclosure, the coating and the drying may be performed while spinning the stent, but may not be limited thereto.

According to an embodiment of the present disclosure, the coating material may include a material selected from the group consisting of a polymer, a drug, a solvent and combinations thereof, but may not be limited thereto.

According to an embodiment of the present disclosure, the polymer may include a polymer selected from the group consisting of polyglycolic acid (PGA), poly-L-lactic acid (PLLA), polylactide-co-glycolide (PLGA), polylactide (PLA), poly-DL-lactic acid (PDLLA), poly-D-lactic acid (PDLA), polydioxanone (PDO), polycaprolactone (PCL), polytrimethylenecarbonate (PTMC), polylactide-co-caprolactone (PLCL), polyhydroxybutyrate (PHB), polyurethane, polyacrylate, polyethylene, polypropylene, polyketone, polystyrene, polyethylene terephthalate, polyphosphorylcholine and combinations thereof, but may not be limited thereto.

According to an embodiment of the present disclosure, the polymer may include a polymer having a molecular weight of from 5,000 MW to 3,000,000 MW, but may not be limited thereto.

According to an embodiment of the present disclosure, the solvent may include a solvent selected from the group consisting of acetic acid, water, ethanol, methanol, propanol, butanol, hexane, methylene chloride, ethyl acetate, propylene glycol, butylene glycol, dipropylene glycol, glycerin, ketone, acetone, dimethyl sulfoxide, dimethylformamide, toluene, tetrahydrofuran, acetonitrile and combinations thereof, but may not be limited thereto.

According to an embodiment of the present disclosure, the drug may include a material selected from the group consisting of sirolimus, everolimus, zotarolimus, xanthorrhizol, docetaxel, cisplatin, camptothecin, paclitaxel, tamoxifen, anastrozole, Gleevec, 5-Fluorouracil (5-FU), fluxuridine, leuprolide, flutamide, zoledronate, doxorubicin, vincristine, gemcitabine, streptozotocin, carboplatin, topotecan, belotecan, irinotecan, vinorelbine, hydroxyurea, valrubicin, retinoic acids, methotrexate, mechlorethamine, chlorambucil, busulfan, doxifluridine, vinblastin, mitomycin, prednisone, testosterone, mitoxantron, aspirin, salicylates, ibuprofen, naproxen, fenoprofen, indomethacin, phenylbutazone, cyclophosphamide, mechlorethamine, dexamethasone, prednisolone, celecoxib, valdecoxib, nimesulide, cortisone, corticosteroid and combinations thereof, but may not be limited thereto.

According to an embodiment of the present disclosure, the stent may be made of a metal and/or a polymer, but may not be limited thereto.

According to an embodiment of the present disclosure, the metal may include a metal selected from the group consisting of Mg, Zn, Fe, Na, K, Ca, Mo, W, Cr, Co, Ti, Ni, Fe and combinations thereof, but may not be limited thereto.

A second aspect of the present disclosure provides a stent manufactured by the method for manufacturing a stent.

The above-described aspects are provided by way of illustration only and should not be construed as liming the present disclosure. Besides the above-described embodiments, there may be additional embodiments described in the accompanying drawings and the detailed description.

Effects of the Invention

According to the above-described means for solving the problems, the method for manufacturing a stent can effectively inhibit a webbing phenomenon through a simple process of simultaneously coating and drying at a temperature in a predetermined range. Also, the method for manufacturing a stent inhibits the webbing phenomenon that a coating material is coated thick on a bent cell portion of the stent so that blood clots in the body do not stick to the stent and a passageway for blood flow can be widened. Therefore, it is possible to effectively treat vascular diseases. Further, it is possible to solve the problem of cytotoxicity caused by an excessive amount of drugs resulting from the webbing phenomenon. Furthermore, by simultaneously coating and drying the stent, it is possible to reduce the time required for drying a drug eluting stent.

According to an embodiment of the present disclosure, the method for manufacturing a stent can effectively inhibit a webbing phenomenon through a simple process of simultaneously coating and drying at a temperature in a predetermined range. Also, the surface roughness of the stent is reduced by inhibiting the webbing phenomenon. Therefore, it is possible to inhibit coarctation and the like.

BEST MODE FOR CARRYING OUT THE INVENTION

Figure 1:
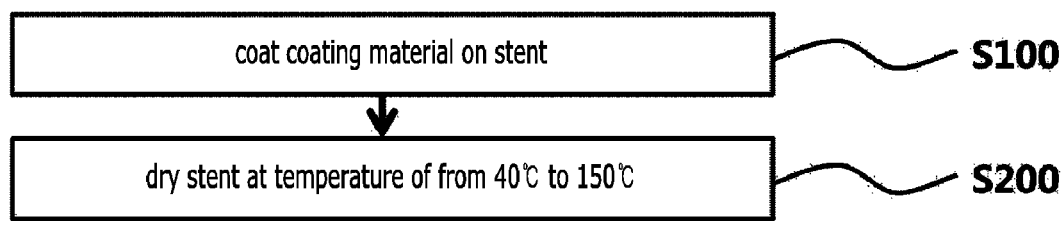
FIG. 1 shows a method for manufacturing a method for manufacturing a stent according to an embodiment of the present disclosure.

Hereinafter, examples of the present disclosure will be described in detail with reference to the accompanying drawings so that the present disclosure may be readily implemented by a person with ordinary skill in the art.

However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the terms "on", "above", "on an upper end", "below", "under", and "on a lower end" that are used to designate a position of one element with respect to another element include both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereafter, a stent and a method for manufacturing the same according to the present disclosure will be described in detail with reference to embodiments, examples, and the accompanying drawings. However, the present disclosure may not be limited to the following embodiments, examples, and drawings.

A first aspect of the present disclosure relates to a method for manufacturing a stent, including: coating a coating material on a stent; and drying the stent at a temperature in the range of from 40° C. to 150° C., and the coating and the drying are simultaneously performed.

FIG. 1 shows a method for manufacturing a method for manufacturing a stent according to an embodiment of the present disclosure.

First, a coating material is coated on a stent (S100).

The process of coating the coating material on the stent may be performed by a method selected from the group consisting of plasma deposition, E-beam deposition, atomic layer deposition (ALD), sputtering, ultrasonic coating, vacuum ion plating, electroplating, dot dipping, spin coating, casting, Langmuir-Blodgett (LB) method, inkjet printing, nozzle printing, slot die coating, doctor blade coating, screen printing, dip coating, gravure printing, reverse offset printing, physical vapor deposition, spray coating, thermal evaporation, vacuum evaporation, chemical vapor deposition and combinations thereof, but may not be limited thereto.

According to an embodiment of the present disclosure, the coating material may include a material selected from the group consisting of a polymer, a drug, a solvent and combinations thereof, but may not be limited thereto.

According to an embodiment of the present disclosure, the polymer may include a polymer selected from the group consisting of polyglycolic acid (PGA), poly-L-lactic acid (PLLA), polylactide-co-glycolide (PLGA), polylactide (PLA), poly-DL-lactic acid (PDLLA), poly-D-lactic acid (PDLA), polydioxanone (PDO), polycaprolactone (PCL), polytrimethylenecarbonate (PTMC), polylactide-co-caprolactone (PLCL), polyhydroxybutyrate (PHB), polyurethane, polyacrylate, polyethylene, polypropylene, polyketone, polystyrene, polyethylene terephthalate, polyphosphorylcholine and combinations thereof, but may not be limited thereto.

According to an embodiment of the present disclosure, the polymer may include a polymer having a molecular weight of from 5,000 MW to 3,000,000 MW, but may not be limited thereto.

According to an embodiment of the present disclosure, the solvent may include a solvent selected from the group consisting of acetic acid, water, ethanol, methanol, propanol, butanol, hexane, methylene chloride, ethyl acetate, propylene glycol, butylene glycol, dipropylene glycol, glycerin, ketone, acetone, dimethyl sulfoxide, dimethylformamide, toluene, tetrahydrofuran, acetonitrile and combinations thereof, but may not be limited thereto.

According to an embodiment of the present disclosure, the drug may include a material selected from the group consisting of sirolimus, everolimus, zotarolimus, xanthorrhizol, docetaxel, cisplatin, camptothecin, paclitaxel, tamoxifen, anastrozole, Gleevec, 5-Fluorouracil (5-FU), fluxuridine, leuprolide, flutamide, zoledronate, doxorubicin, vincristine, gemcitabine, streptozotocin, carboplatin, topotecan, belotecan, irinotecan, vinorelbine, hydroxyurea, valrubicin, retinoic acids, methotrexate, mechlorethamine, chlorambucil, busulfan, doxifluridine, vinblastin, mitomycin, prednisone, testosterone, mitoxantron, aspirin, salicylates, ibuprofen, naproxen, fenoprofen, indomethacin, phenylbutazone, cyclophosphamide, mechlorethamine, dexamethasone, prednisolone, celecoxib, valdecoxib, nimesulide, cortisone, corticosteroid and combinations thereof, but may not be limited thereto.

According to an embodiment of the present disclosure, the stent may be made of a metal and/or a polymer, but may not be limited thereto.

According to an embodiment of the present disclosure, the metal may include a metal selected from the group consisting of Mg, Zn, Fe, Na, K, Ca, Mo, W, Cr, Co, Ti, Ni, Fe and combinations thereof, but may not be limited thereto.

Then, the stent is dried at a temperature in the range of from 40° C. to 150° C. (S200).

If the stent is dried at a temperature of less than 40° C., a webbing phenomenon may occur. If the stent is dried at a temperature of more than 150° C., the coating material coated on the stent may crack.

The coating S100 and the drying S200 may be simultaneously performed, but may not be limited thereto.

According to an embodiment of the present disclosure, the coating and the drying may be simultaneously performed to inhibit a webbing phenomenon, but may not be limited thereto.

When the drying S200 is performed after the coating S100 is completed, the stent with a solution remaining in a cell portion may be dried so that a webbing phenomenon may occur.

According to an embodiment of the present disclosure, the method for manufacturing a stent can effectively inhibit a webbing phenomenon through a simple process of simultaneously coating and drying at a temperature in a predetermined range. Also, the surface roughness of the stent is reduced by inhibiting the webbing phenomenon. Therefore, it is possible to inhibit coarctation and the like.

Also, the method for manufacturing a stent inhibits the webbing phenomenon that a coating material is coated thick on a bent cell portion of the stent so that blood clots in the body do not stick to the stent and a passageway for blood flow can be widened. Therefore, it is possible to effectively treat vascular diseases.

In addition, it is possible to solve the problem of cytotoxicity caused by an excessive amount of drugs resulting from the webbing phenomenon.

According to an embodiment of the present disclosure, the coating and the drying may be performed while spinning the stent, but may not be limited thereto.

Figure 2:
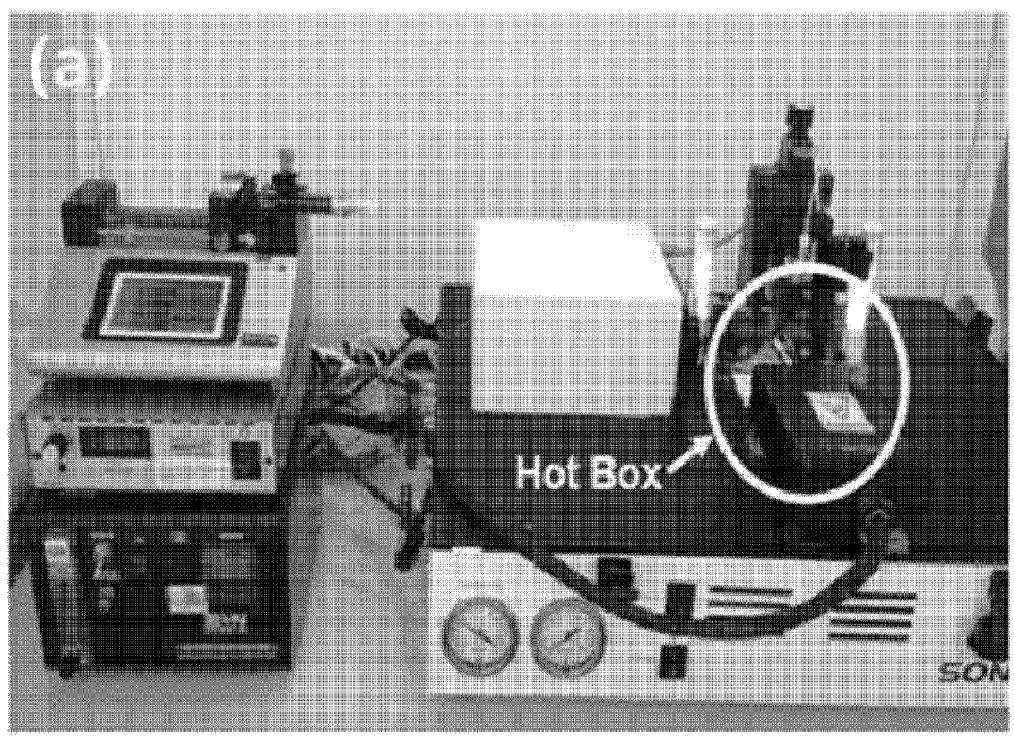
FIG. 2 is a photograph (a) and a schematic diagram (b), respectively, of a stent coating apparatus according to an embodiment of the present disclosure.
Figure 2:
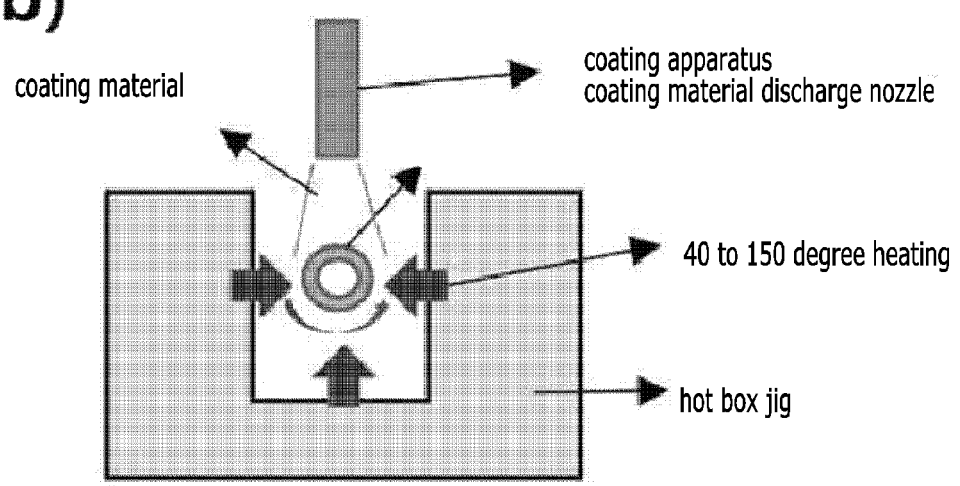

(a) and (b) of FIG. 2 are a photograph and a schematic diagram, respectively, of a stent coating apparatus according to an embodiment of the present disclosure.

Specifically, (b) of FIG. 2 is a schematic diagram showing a side surface of the stent coating apparatus.

Referring to FIG. 2, while the coating material is sprayed from a coating material discharge nozzle located at an upper end of the stent, the coating material is dried in a hot box at a temperature in the range of from 40° C. to 150° C. Here, the stent is spun so that the sprayed coating material can be evenly coated on the stent.

The coating and the drying are performed while spinning the stent. Therefore, the coating material can be evenly coated on the stent.

A second aspect of the present disclosure relates to a stent manufactured by the method for manufacturing a stent.

Detailed descriptions of the stent according to the second aspect of the present disclosure, which overlap with those of the first aspect of the present disclosure, are omitted hereinafter, but the descriptions of the first aspect of the present disclosure may be identically applied to the second aspect of the present disclosure, even though they are omitted hereinafter.

When the stent according to an embodiment of the present disclosure is manufactured, the coating material does not remain in the cell portion of the stent by inhibiting a webbing phenomenon. Therefore, coarctation caused by reaction between the coating material and blood does not occur.

The stent may have a dilatation rate of less than 120 seconds, but may not be limited thereto.

If the stent has a dilatation rate of more than 120 seconds, the stent may disrupt the flow of blood, which may cause a shock.

Hereinafter, the present disclosure will be described in more detail with reference to examples. The following examples are provided only for explanation, but do not intend to limit the scope of the present disclosure.

EXAMPLE

First, a polymer solution was prepared by dispersing a poly-L-lactic acid (PLLA) polymer in ethanol. The polymer solution was coated on stents by spray coating and dried at temperatures of 40° C., 80° C., 100° C. and 120° C., respectively, at the same time.

Comparative Example 1

First, a polymer solution was prepared by dispersing a poly-L-lactic acid (PLLA) polymer in ethanol. The polymer solution was coated on a stent by spray coating and dried at a temperature of 160° C. at the same time.

Comparative Example 2

First, a polymer solution was prepared by dispersing a poly-L-lactic acid (PLLA) polymer in ethanol. The polymer solution was coated on stents by spray coating. The stents coated with the polymer solution were dried at temperatures of 80° C., 100° C. and 120° C., respectively.

[Test Example]

The characteristics of the stents manufactured according to Example and Comparative Examples were examined, and the results thereof are as shown in FIG. 3 to FIG. 6.

Figure 3:
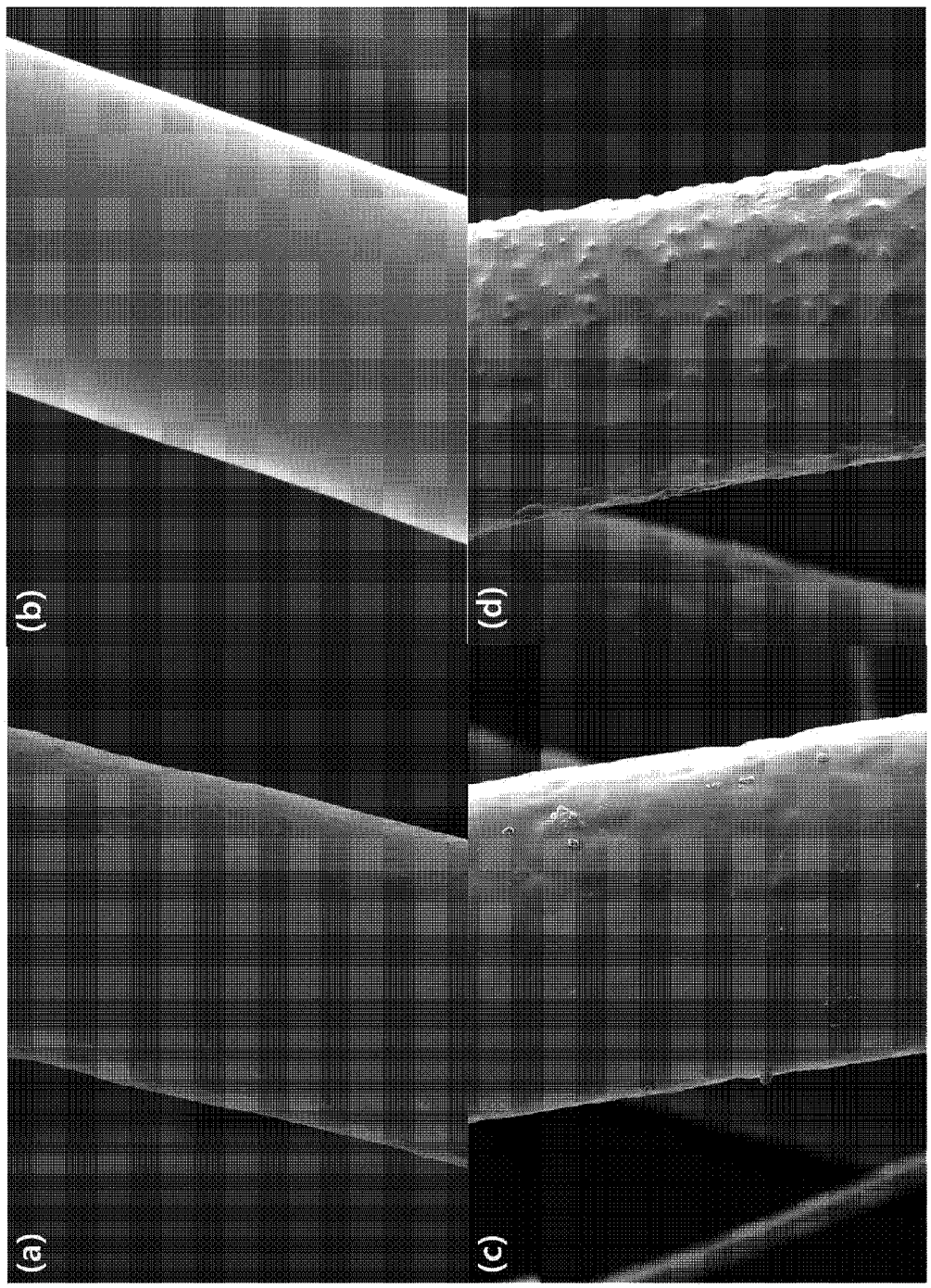
FIG. 3 is scanning electron microscope (SEM) images of the surfaces of stents dried at temperatures of 40° C., 80° C., 100° C. and 120° C., respectively, according to an example of the present disclosure.

(a) to (d) of FIG. 3 are scanning electron microscope (SEM) images of the surfaces of stents dried at temperatures of 40° C., 80° C., 100° C. and 120° C., respectively, according to an example of the present disclosure.

Figure 4:
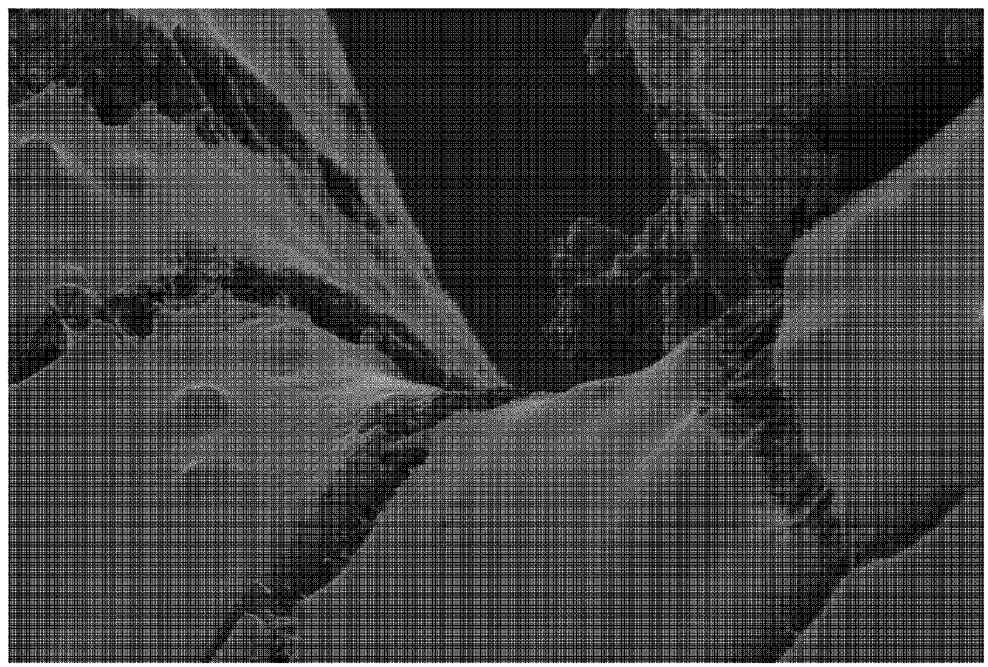
FIG. 4 is a scanning electron microscope (SEM) image of the surface of a stent manufactured according to a comparative example of the present disclosure.

FIG. 4 is a scanning electron microscope (SEM) image of the surface of a stent manufactured according to a comparative example of the present disclosure.

Specifically, FIG. 4 is a photograph of the surface of the stent manufactured according to Comparative Example 1. Even when coating and drying are simultaneously performed, if drying is performed at a temperature of 160° C. higher than 150° C., the polymer cracks.

Figure 5:
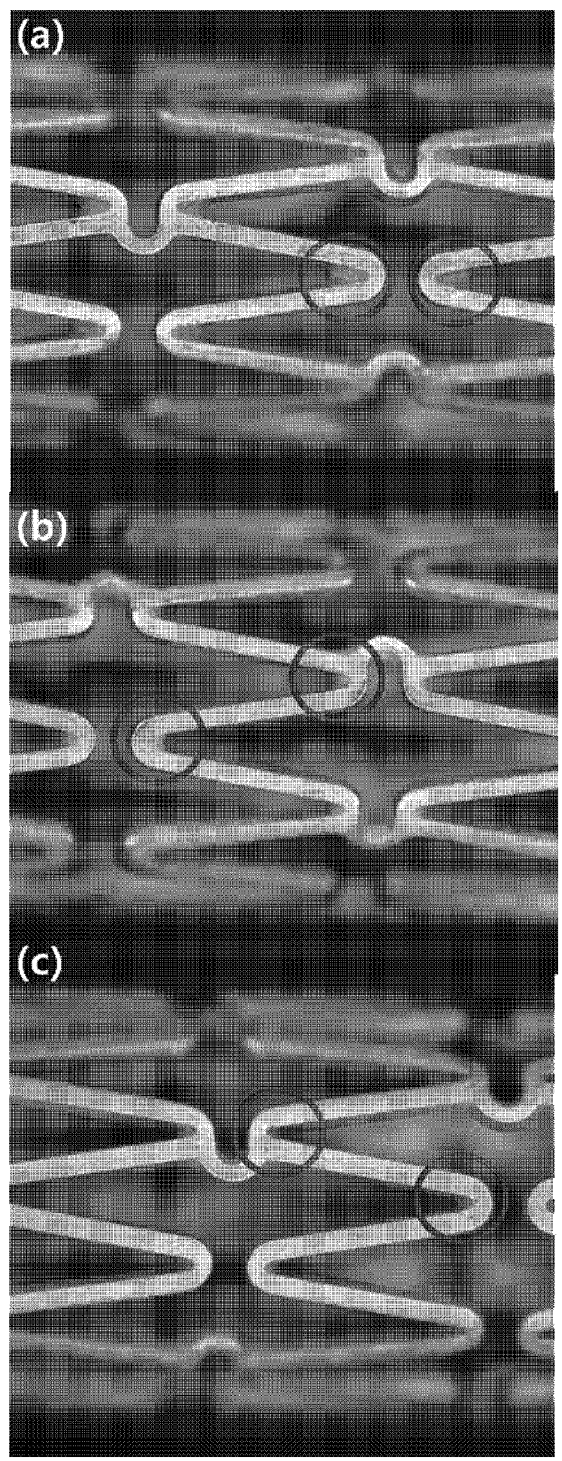
FIG. 5 is scanning electron microscope (SEM) images of stents dried at temperatures of 80° C., 100° C. and 120° C., respectively, according to a comparative example of the present disclosure.

(a) to (c) of FIG. 5 are scanning electron microscope (SEM) images of stents dried at temperatures of 80° C., 100° C. and 120° C., respectively, according to a comparative example of the present disclosure.

According to the result shown in FIG. 5, it can be seen that when the polymer solution is coated and then dried, a webbing phenomenon occurs.

Figure 6:
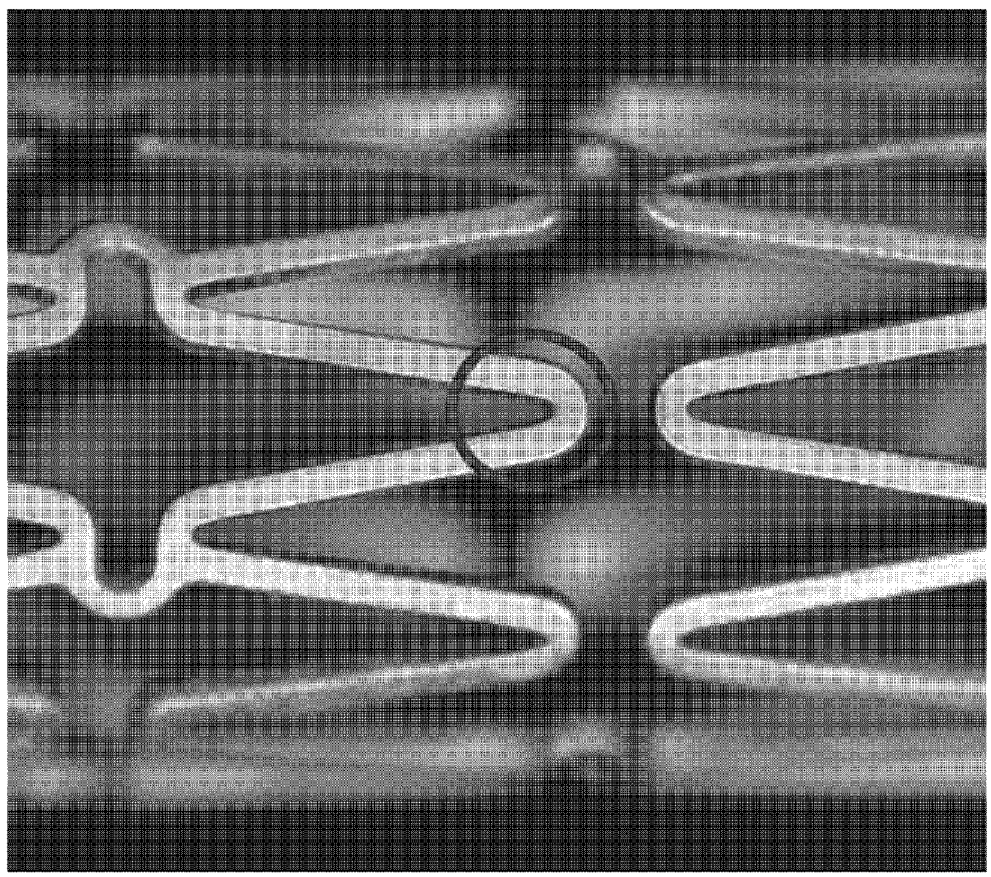
FIG. 6 is a scanning electron microscope (SEM) image of a stent manufactured according to an example of the present disclosure.

FIG. 6 is a scanning electron microscope (SEM) image of a stent manufactured according to an example of the present disclosure.

Specifically, FIG. 6 is an SEM image of a stent manufactured by simultaneously coating and drying the polymer solution at a temperature of 80° C.

According to the result shown in FIG. 6, it can be seen that a webbing phenomenon does not occur when coating and drying are simultaneously performed.

Particularly, according to the result of comparison between (a) of FIG. 5 and FIG. 6, it can be seen that drying was performed at the same temperature of 80° C., but a webbing phenomenon did not occur when coating and drying were simultaneously performed as shown in FIG. 6, whereas a webbing phenomenon occurred in the case shown in (a) of FIG. 5.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A method for manufacturing a stent, the method comprising:
    preparing a hot container maintained at a temperature in a range of from 40° C. to 150° C.;
    placing a stent inside the hot container and spinning the stent to heat the stent; and
    spraying a coating material through a nozzle towards the stent placed and being spun inside the hot container, thereby being able to perform coating of the coating material and drying of a coated material, simultaneously, to inhibit a webbing phenomenon.

2. The method for manufacturing a stent of claim 1, wherein the coating material includes a polymer, a drug, and a solvent.

3. The method for manufacturing a stent of claim 2, wherein the polymer includes a polymer selected from the group consisting of polyglycolic acid (PGA), poly-L-lactic acid (PLLA), polylactide-co-glycolide (PLGA), polylactide (PLA), poly-DL-lactic acid (PDLLA), poly-D-lactic acid (PDLA), polydioxanone (PDO), polycaprolactone (PCL), polytrimethylenecarbonate (PTMC), polylactide-co-caprolactone (PLCL), polyhydroxybutyrate (PHB), polyurethane, polyacrylate, polyethylene, polypropylene, polyketone, polystyrene, polyethylene terephthalate, polyphosphorylcholine and combinations thereof.

4. The method for manufacturing a stent of claim 3, wherein the polymer includes a polymer having a molecular weight of from 5,000 MW to 3,000,000 MW.

5. The method for manufacturing a stent of claim 2, wherein the solvent includes a solvent selected from the group consisting of acetic acid, water, ethanol, methanol, propanol, butanol, hexane, methylene chloride, ethyl acetate, propylene glycol, butylene glycol, dipropylene glycol, glycerin, ketone, acetone, dimethyl sulfoxide, dimethylformamide, toluene, tetrahydrofuran, acetonitrile and combinations thereof.

6. The method for manufacturing a stent of claim 2, wherein the drug includes a material selected from the group consisting of sirolimus, everolimus, zotarolimus, xanthorrhizol, docetaxel, cisplatin, camptothecin, paclitaxel, tamoxifen, anastrozole, Gleevec, 5-Fluorouracil (5-FU), fluxuridine, leuprolide, flutamide, zoledronate, doxorubicin, vincristine, gemcitabine, streptozotocin, carboplatin, topotecan, belotecan, irinotecan, vinorelbine, hydroxyurea, valrubicin, retinoic acids, methotrexate, mechlorethamine, chlorambucil, busulfan, doxifluridine, vinblastin, mitomycin, prednisone, testosterone, mitoxantron, aspirin, salicylates, ibuprofen, naproxen, fenoprofen, indomethacin, phenylbutazone, cyclophosphamide, mechlorethamine, dexamethasone, prednisolone, celecoxib, valdecoxib, nimesulide, cortisone, corticosteroid and combinations thereof.

7. The method for manufacturing a stent of claim 1, wherein the stent is made of a metal and/or a polymer.

8. The method for manufacturing a stent of claim 7, wherein the metal includes a metal selected from the group consisting of Mg, Zn, Fe, Na, K, Ca, Mo, W, Cr, Co, Ti, Ni, Fe and combinations thereof.

* * * * *